(12) United States Patent
Bumbalough et al.

(10) Patent No.: US 9,554,892 B2
(45) Date of Patent: Jan. 31, 2017

(54) OPHTHALMIC LENSES WITH ENHANCED SURFACE AND METHODS OF FABRICATION THEREOF

(71) Applicant: Abbott Medical Optics Inc., Santa Ana, CA (US)

(72) Inventors: Timothy R. Bumbalough, Fullerton, CA (US); Daniel G. Brady, San Juan Capistrano, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 93 days.

(21) Appl. No.: 14/509,620

(22) Filed: Oct. 8, 2014

(65) Prior Publication Data

US 2015/0142109 A1    May 21, 2015

Related U.S. Application Data

(62) Division of application No. 12/785,255, filed on May 21, 2010, now abandoned.

(60) Provisional application No. 61/180,822, filed on May 22, 2009.

(51) Int. Cl.
*A61F 2/16* (2006.01)

(52) U.S. Cl.
CPC .......... *A61F 2/1613* (2013.01); *A61F 2/1648* (2013.01); *A61F 2002/1681* (2013.01); *A61F 2002/1699* (2015.04); *A61F 2210/0076* (2013.01); *A61F 2250/0053* (2013.01)

(58) Field of Classification Search
CPC .................. A61F 2/1613; A61F 2/1648; A61F 2250/0053; A61F 2210/0076; A61F 2/1624
See application file for complete search history.

(56) References Cited

U.S. PATENT DOCUMENTS

| | | |
|---|---|---|
| 4,731,079 A | 3/1988 | Stoy |
| 6,609,793 B2 | 8/2003 | Norrby et al. |
| 2002/0188351 A1 | 12/2002 | Laguette |
| 2008/0161913 A1 | 7/2008 | Brady et al. |
| 2008/0161914 A1 | 7/2008 | Brady et al. |
| 2009/0088839 A1 | 4/2009 | Hu et al. |
| 2009/0163602 A1 | 6/2009 | Hu et al. |

(Continued)

FOREIGN PATENT DOCUMENTS

| | | |
|---|---|---|
| DE | 3428895 A1 | 2/1986 |
| WO | WO-02088830 A1 | 11/2002 |

OTHER PUBLICATIONS

Apple D.J., et al., Eds., "Intraocular Lenses: Evolution, Designs, Complications and Pathology," in: New Concepts in Intraocular Lens Implantation, Williams & Wilkins publisher, 1989, pp. 204-221.

(Continued)

*Primary Examiner* — Howie Matthews
(74) *Attorney, Agent, or Firm* — Abbott Medical Optics Inc.

(57) ABSTRACT

An ophthalmic lens for providing enhanced vision includes a finished optic comprising a base optic and a membrane. The base optic has an anterior surface and an opposing posterior surface, at least one of the surfaces having a first value of a surface quality parameter. The base optic also includes a membrane including an inner surface and an outer surface, the inner surface covering one or more of the surfaces of the base optic. The outer surface has a second value of the surface quality parameter, wherein the second value is greater than the first value.

23 Claims, 4 Drawing Sheets

(56) References Cited

U.S. PATENT DOCUMENTS

2009/0164009 A1  6/2009  Hu et al.

OTHER PUBLICATIONS

International Preliminary Report on Patentability and Written Opinion for Application No. PCT/US2010/035832, mailed on Nov. 22, 2011, 7 pages.
International Search Report for Application No. PCT/US2010/035832, mailed on Sep. 22, 2010, 3 pages.
Machine Translation of DE3428895A1 Obtained from EPO Patent Translate Apr. 21, 2013, pp. 1-6.
Marsack J.D., et al., "Metrics of Optical Quality Derived from Wave Aberrations Predict Visual Performance," Journal of Vision, 2004, vol. 4 (4), pp. 322-328.
Van Meeteren A., "Calculations on the Optical Modulation Transfer Function of the Human Eye for White Light," Optica Acta, 1974, vol. 21 (5), pp. 395-412.
Villegas E.A., et al., "Correlation between Optical and Psychophy, Sical Parameters as a Function of Defocus," Optometry and Vision Science, 2002, vol. 79 (1), pp. 60-67.

OPHTHALMIC LENSES WITH ENHANCED SURFACE AND METHODS OF FABRICATION THEREOF

CROSS-REFERENCE TO RELATED APPLICATIONS

This application claims priority to U.S. application Ser. No. 12/785,255, filed on May 21, 2010, now abandoned, which claims priority to U.S. Provisional Application No. 61/180,822, filed on May 22, 2009, the entire contents of both of which are incorporated herein by reference.

BACKGROUND OF THE INVENTION

Field of the Invention

The present invention relates generally to ophthalmic lenses and methods of making ophthalmic lenses, more specifically to ophthalmic lenses formed with enhanced outer surfaces.

Description of the Related Art

Intraocular lenses (IOLs) are used to replace or supplement the natural lens of an eye. Accommodative intraocular lenses (AIOLs) may be used to provide a range of optical powers or optic positions that at least partially restore the ability to focus on objects over a range of distances. AIOLs are typically more difficult to produce due to increased performance demands compared to more traditional monofocal or multifocal intraocular lenses.

For example, an AIOL may include a more complex support structure than the relatively simple haptics of more traditional monofocal or multifocal IOLs, which have relatively simple design requirements—for example to keep an optic centered and stable within an eye of a subject. By contrast, the structures for supporting the optic of an AIOL may be required to precisely move an optic and/or to change the shape of the optic. In order to provide a reasonable range of accommodation, AIOL supporting structures must also be able to efficiently transfer relatively small amounts of ocular forces to provide the maximum amount of optic movement and/or shape change. In addition, optic materials for AIOLs may be required to be relatively soft in order to enhance the ability of the optic to change shape. By contrast, the associated support structure material may be required to be much stiffer to facilitate transfer of ocular forces. These differences in material properties between the optic and support structure can make construction of a unitary IOL difficult. As a result of all of these requirements, it has been found that it is generally more difficult to fabricate an AIOL that has the same high optical performance common with more traditional monofocal or multifocal IOLs.

Accordingly, other methods of producing intraocular lenses in general, and accommodating intraocular lenses more specifically, are needed.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the present invention. The drawings include the following figures.

DETAILED DESCRIPTION OF THE DRAWINGS

Figure 1:
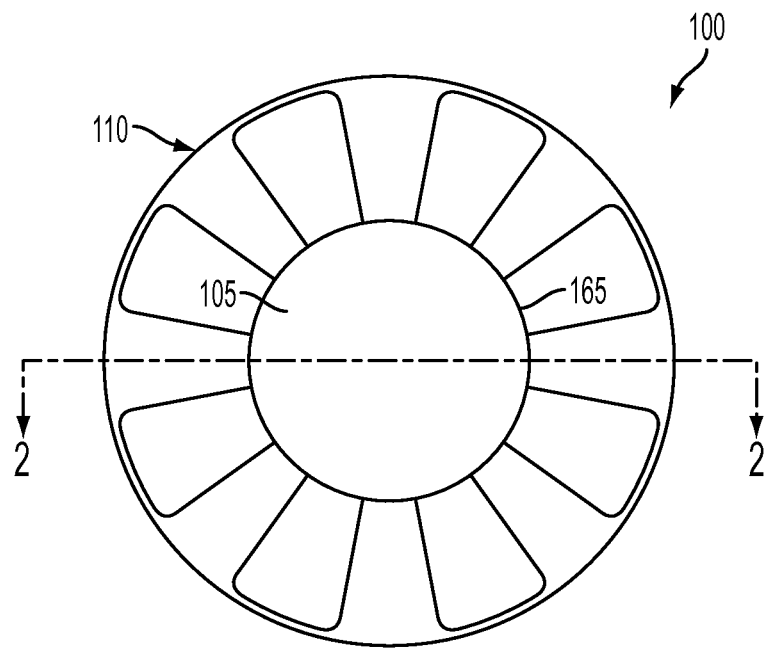
FIG. 1 is a top view of an intraocular lens according to an embodiment of the present invention.

The present invention is generally directed to lenses and methods of making and using such lenses, that provide enhanced optical performance in ophthalmic applications, for example, where complex lens support structures make optical requirements more difficult to attain. Embodiments of the present invention may find particular use in the field of accommodative optics, where relatively complex design requirements make it more difficult to produce optics delivering both high quality optical performance and a required amount of accommodative change. While the present description below is generally directed to accommodating intraocular lenses (AIOLs), embodiments of the present invention may include other types of lenses or optics, for example, other types of ophthalmic lenses such as monofocal or multifocal intraocular lenses, toric lenses, optically optimized lenses, contact lenses, corneal implants, and the like.

Embodiments of the present invention are directed to intraocular lenses that meet high optical performance requirements, even where complex support structures and/or difficult material challenges have traditionally made this more difficult. In the area of AIOLs, it has been found that when a soft optic material is molded around a pre-existing optic positioning device or support structure made of a different material, differences in shrinkage rates may cause deformation of optic surfaces that can compromise optical performance. The amount of unwanted optic deformation may be amplified even more when the optic/support structure combination is further processed to extract unwanted contaminants from the intraocular lens. Accordingly, AIOLs according to embodiments of the present invention are able to overcome such challenges.

In certain embodiments, it has been discovered that the optical quality of an optic may be restored after molding and/or extraction of contaminants by forming a thin membrane or film over one or both optical surfaces of a base optic. In this manner, the shape and surface quality of the membrane surfaces are made superior to original surfaces of the base optic. By carefully configuring the membrane with a small thickness or volume, any subsequent shrinkage is rendered negligible, resulting in an optic that has superior optical performance compared to the originally molded base optic.

In some embodiments, the application of a membrane or film to a base optic, can enhance performance in other ways besides simply improving the optical quality of the optic surface. Examples of such enhanced performance include, but are not limited to, provision of a multifocal optic surface (either refractive or diffractive) from a monofocal base optic, provision of an aspheric optic from a spherical base optic, or provision of chromatic correcting optic (e.g., by application of a diffractive profile to a base optic or by formation of a secondary optic from a material having a different refractive index and/or Abbe number than that of the base optic). Additionally or alternatively, the membrane or film may be made of a different material, or have different material properties, than the underlying base optic. For example, all or portions of the membrane or film may have a different stiffness, tensile strength, modulus, lubricity, tackiness than the base optic, and/or optical properties such as transmission or UV cut-off.

Figure 2:
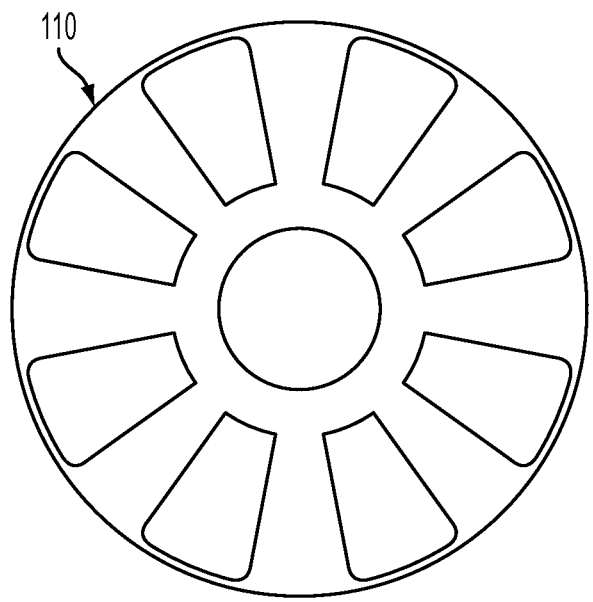
FIG. 2 is a top view of a support structure of the intraocular lens shown in FIG. 1 prior to attachment of an associated optic portion.
Figure 3:
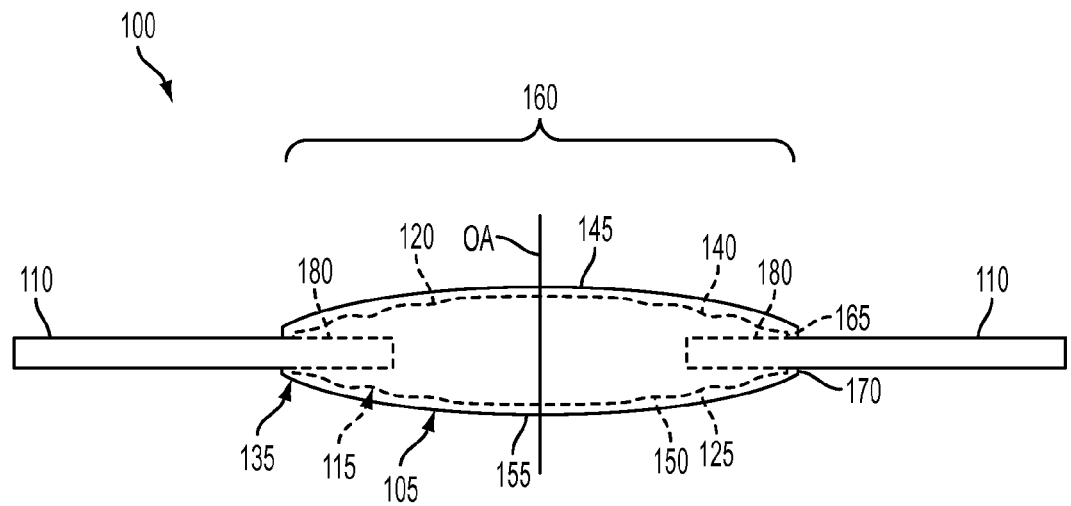
FIG. 3 is a side view of the intraocular lens shown in FIG. 1.

Referring to FIGS. 1-3, an intraocular lens 100 according to an embodiment of the present invention comprises a finished optic 105 and a support structure or positioning device 110. The finished optic 105 is disposed about an optical axis OA and includes a base optic 115 having an anterior surface 120 and an opposing posterior surface 125. The finished optic 105 is formed when a layer or shell 135 is applied or attached to base optic 115. Beneficially, intraocular lens 100 may be configured to be an accommodating intraocular lens in which a relatively finished optic 105 changes shape in response to an ocular force.

The shell 135 comprises an anterior membrane or film 140 with an outer surface 145 that covers anterior surface 120 of base optic 115. The shell 135 further comprises a posterior membrane or film 150 with an outer surface 155 covering posterior surface 125 of base optic 115. Membranes 140, 150 also include inner surfaces that contact, and generally conform to, anterior and posterior surfaces 120, 125, respectively, of base optic 115. The inner surfaces of membranes 140, 150 may adhere to surfaces 120, 125 in such a way that there is no, or little, air or other material between the membrane inner surfaces and surfaces 120, 125 of the base optic 115. In certain embodiments, finished optic 105 includes only one of the membranes 140, 150. As used herein, the term "membrane" means a sheet or layer of a material that has a maximum linear extent (i.e. diameter) that is much greater than the maximum thickness of the layer of material. In this context, the term "much greater" means the layer of material has a maximum extent that is at least 10 times greater than the maximum thickness. In some embodiments, the membrane may have a maximum extent that is at least 20 times, 50 times, or 100 times greater than the maximum thickness of the layer of material.

Base optic 115 may further comprise a clear aperture 160 and a peripheral edge or wall 165 that joins or connects anterior and posterior surfaces 120, 125 of base optic 115. As used herein, the term "clear aperture" means the opening of a lens or optic that restricts the extent of a bundle of rays from a collimated source or a distant light source that can be imaged or focused by the lens or optic. The clear aperture is usually circular and specified by its diameter. Thus, the clear aperture represents the full extent of the lens or optic that is usable in forming an image or for focusing light from a distant point source. In some embodiments, the clear aperture has the same or substantially the same diameter as the optic. Alternatively, the diameter of the clear aperture may be smaller than the diameter of the optic, for example, due to the presence of a glare or PCO reducing structure disposed about a peripheral region of the optic.

Shell 135 may additionally comprise a peripheral edge cover 170 that covers peripheral edge 165. Peripheral edge cover 170 circumferentially extends along peripheral edge 165 and extends between or joins anterior membrane 140 and posterior membrane 150 of finished optic 105. Peripheral edge cover 170 may have a thickness (i.e., in a radial direction from the optical axis OA) that is equal to, or approximately equal to, a thickness of either or both membranes 140, 150. Alternatively, peripheral cover 170 may have a thickness that is greater than a thickness of either or both membranes 140, 150, for example, 50% greater than the thickness of membranes 140, 150, or 100% greater than the thickness of membranes 140, 150.

In the illustrated embodiment, support structure 110 optionally includes protruding portions 180 that are disposed within base optic 115. Protruding portions 180 may be configured to allow ocular forces produced by the ciliary muscle and/or capsular bag of an eye to be more effectively transferred to central portions of finished optic 105, thereby increasing the accommodative ranges of intraocular lens 100. Such designs are discussed in greater detail in U.S. Patent Application Numbers 2008-0161913 and 2008-0161914, both of which are herein incorporated by reference in their entirety.

Base optic 115 and membranes 140, 150 may generally be made of any of the various materials known in the art including, but not limited to, silicone polymeric materials, acrylic polymeric materials, hydrogel-forming polymeric materials (e.g., polyhydroxyethylmethacrylate, polyphosphazenes, polyurethanes, polystyrene, and mixtures thereof), and the like. Other formulations of silicone, acrylic, or mixtures thereof are also anticipated. Selection parameters for suitable lens materials are well known to those of skill in the art. See, for example, David J. Apple, et al., Intraocular Lenses: Evolution, Design, Complications, and Pathology, (1989) William & Wilkins, which is herein incorporated by reference in its entirety. Support structure 110 may be constructed of more rigid materials including, but not limited to, polymeric materials such as silicone polymeric materials, acrylic polymeric materials, low water content hydrophilic, hydrogel-forming polymeric materials, polypropylene, polymethylmethacrylate PMMA, polycarbonates, polyamides, polyimides, polyacrylates, 2-hydroxymethylmethacrylate, poly (vinylidene fluoride), polytetrafluoroethylene, polystyrene, and the like.

In an embodiment, membranes 140, 150 may be made of a material that has a similar or the same modulus as the base optic 115. In an embodiment, membranes 140, 150 may be made of a material that has a higher modulus than the base optic 115 and/or of a material with lower extractables than base optic 115. Using a material having a higher modulus and/or lower extractables for membranes 140, 150 may result in less shrinkage of the material during fabrication. Less or minimal shrinkage of membranes 140, 150 may result in an improved surface and optical quality of finished optic 105, which is described further herein.

Foldable/deformable materials are particularly advantageous since lenses made from such deformable materials may be rolled, folded or otherwise deformed and inserted into the eye through a small incision. Lens materials may have a refractive index allowing a relatively thin and flexible optic section, for example, having a thickness in the range of about 150 microns to about 3000 microns. Finished optic may have a diameter from 4 mm or less to 7 mm or more, generally from about 5.0 mm to about 6.0 mm. Base optic 115 and/or membranes include 140, 150 may also include more advanced formulations, for example to provide material properties desirable in AIOLs. Examples of suitable materials are disclosed in U.S. Patent Application Publication Number 2009/0088839 and in co-pending U.S. patent application Ser. No. 11/963,351 (U.S. Publication No. 2009/

0163602) and Ser. No. 12/205,703 (U.S. Publication No. 2009/0164009)—all these disclosures being incorporated by reference in their entirety.

In some embodiments, the surface and/or optical quality of outer surfaces 145, 155 of membranes 140, 150 may be generally higher than the surface or optical quality of surfaces 120, 125 of base optic 115. For example, outer surface 145 of anterior membrane 140 may be generally smoother than anterior surface 120 of base optic 115, while outer surface 155 of posterior membrane 150 may be generally smoother than posterior surface 120 of base optic 115. Moreover, the optical quality of outer surface 145 of anterior membrane 140 may be higher than the optical quality of anterior surface 120 of base optic 115, while the optical quality of outer surface 155 of posterior membrane 150 may be higher than the optical quality of posterior surface 120 of base optic 115.

The refractive index of films 140, 150 and/or protruding portions 180 may be equal to, or about equal to, the refractive index of base optic 115. As used herein, the refractive index of two materials are equal to one if they have the same refractive index at one or more wavelengths within the visible spectrum (i.e., a wavelength from 400 nm to 700 nm). As used herein, the refractive indices of two materials are "about equal" to one another if their refractive indices are within 0.4% at one or more wavelengths within the visible spectrum, preferably within 0.1% at one or more wavelengths within the visible spectrum. By matching the refractive indices, the amount of reflections between surfaces may be significantly reduced. In such embodiments, the Abbe number of films 140, 150 and/or protruding portions 180 may also be equal to, or about equal to, the Abbe number of base optic 115. As used herein, the Abbe numbers of two materials are "about equal" to one another if their Abbe numbers are within 2.0 of one another, preferably within 0.5 of one another. In an embodiment, matching support structure 110 to base optic 115 is tighter or closer than matching films 140, 150 to base optic 115. In other words, there is less difference in refractive indices or Abbe numbers between support structure 110 to base optic 115 than between films 140, 150 to base optic 115.

In some embodiments, the refractive index and/or the Abbe number of membranes 140, 150 are different from the refractive index and/or Abbe number of base optic 115. For example, a difference in refractive index and/or the Abbe number may be utilized to reduce chromatic aberrations of finished optic 105. In such embodiments, one or both films 140, 150 may be replaced by a second optic that is relatively thick and configured, in combination with base optic 115, to reduce a chromatic aberration or achromatic aberration of the intraocular lens 100 itself or of an eye into which intraocular lens 100 is placed. In an embodiment, the UV cut-off of films 140, 150 are different from the base optic 115. In an embodiment, the percent transmission across the visible spectrum should be substantially equivalent between support structure 110 and films 140, 150.

In some embodiments, one or both films 140, 150 may define a plurality of echelettes of a diffractive grating. The diffractive grating may be a monofocal diffractive grating, for example configured to reduce a chromatic aberration of finished optic 105 and/or of an eye into which intraocular lens 100 is placed. Alternatively, the diffractive grating may be a multifocal diffractive grating, for example configured to provide both distant vision and near vision, to provide both distant and intermediate vision, or to provide an extended depth of focus. In certain embodiments, one of the outer surfaces 145, 155 has a diffractive grating, while the opposite surface 155, 145 is part of a second optic as describe above for reducing a chromatic or achromatic aberration.

In certain embodiment, all or portions of shell 135 may be made of the same material as base optic as base optic 115. This may be a useful configuration for matching the refractive indices and/or Abbe numbers between base optic 115 any or all of membrane 140, membrane 150, and/or peripheral edge cover 170. Alternatively, any or all of membrane 140, membrane 150, and/or peripheral edge cover 170 may be made of a different material than the material used to form base optic 115 or of the same material that is processed in a different manner to provide a different physical, mechanical, or optical property. For example, any or all of membrane 140, membrane 150, and/or peripheral edge cover 170 may be made of a material having a different stiffness, tensile strength, modulus, lubricity, and/or tackiness than base optic 115. As another example, either or both of membranes 140, 150 may be made of a material having a different refractive index and/or Abbe number, for example, to provide a refractive achromat finished optic 105. In some embodiments, base optic 115 is made from a first material having a first value of a property and one or more of elements 140, 150, 170 are made from a second material having a second value of the property, wherein the first value is greater than the second value. The difference in the first and second values may be greater than 2%, greater than 5%, greater than 10%, or even greater than 25%.

Where applicable, in any or all of the embodiments of the previous paragraph, rather than using a material that is different from base optic 115, the same material, or a common polymeric material, may be used with any or all of membrane 140, membrane 150, and/or peripheral edge cover 170. In such embodiments, the material of elements 140, 150, and/or 170 may be processed in a different way than the material of base optic 115 to provide a different physical, mechanical, or optical property. Alternatively, the material of elements 140, 150, and/or 170 may be made of a common polymeric material to that of base optic 115. As used herein, a "common polymeric material" refers to similarity of material composition between two objects or portions of an object, wherein the two objects or portions consist essentially of the same base polymer chain or have at least 50% w/w of the same base polymer chain, or 75% w/w of the same base polymer chain, or 85% w/w of the same base polymer chain, or 90% w/w of the same base polymer chain, or 95% w/w of the same base polymer chain, and, when present, the same cross-linking agent.

Any or all of elements 140, 150, and/or 170 may be affixed or joined to base optic 115. In some embodiments, an adhesive material is disposed between base optic 115 and any or all of elements 140, 150, and/or 170, for example, to join, glue, or couple any or all of elements 140, 150, and/or 170 to base optic 115. In some embodiments, base optic 115 and any or all of elements 140, 150, and/or 170 form a unitary or one-piece structure.

Figure 4:
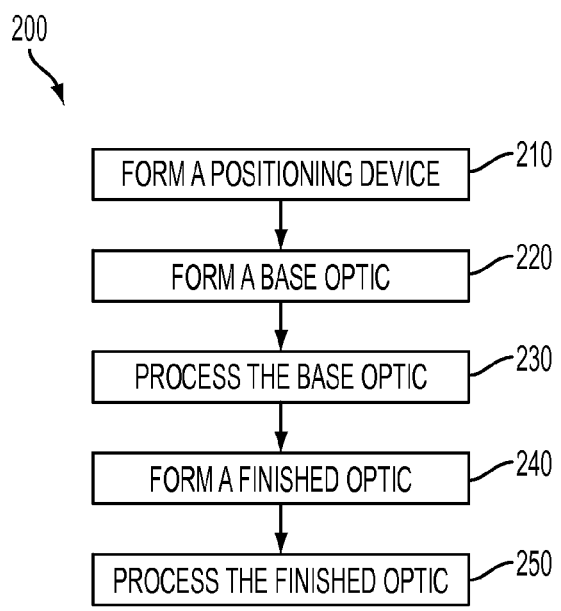
FIG. 4 is a block diagram of a method of making an ophthalmic lens according to an embodiment of the present invention.

Referring to FIG. 4, a method 200 of making an intraocular lens comprises an element 210 of forming a positioning device or support structure of an intraocular lens and an element 220 of forming a base optic of the intraocular lens. Method 200 further comprises an element 230 of processing the base optic and an element 240 of subsequently forming a finished optic. The method 200 also comprises an element 250 of further processing the finished optic. In certain embodiments, one or more of the elements of the method 200 are left out (e.g., element 230 and/or element 250). In certain embodiments, a tumbling step may be added to method 200 after element 210, 220, 230, 240, and/or 250, e.g. tumbling support structure 110 to remove flash before molding base optic 115.

In an embodiment, the radius of curvature of films 140, 150 may be substantially equivalent to the surface shape of base optic 115. Alternatively, due to the processing in element 240, a spherical shape difference between films 140, 150 and base optic 115 may result in an aspheric surface to improve performace.

Figure 6:
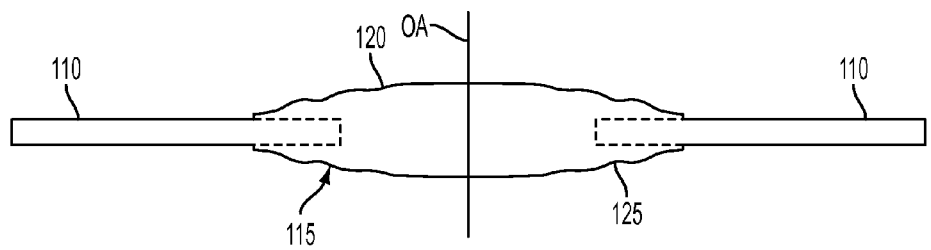
FIG. 6 is a side view of the support structure and a base optic of the intraocular lens shown in FIG. 5 after further processing.
Figure 7:
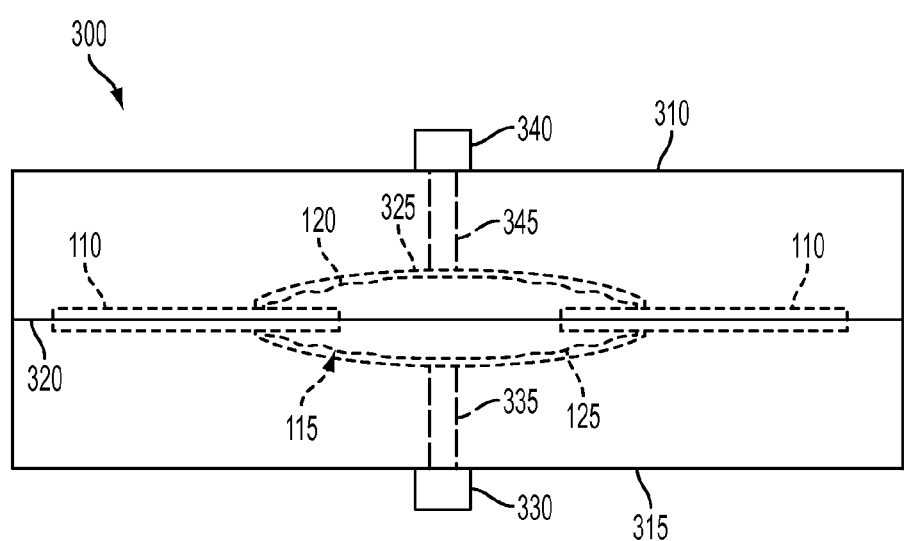
FIG. 7 is a side view of a mold for fabricating the intraocular lens shown in FIG. 1.

With additional reference to FIGS. 5-7, an exemplary embodiment of the use of method 200 for fabricating the intraocular lens 100 will be discussed. Referring again to FIG. 2, fabrication of intraocular lens 100 begins with element 210 of method 200, comprising forming support structure 110. Support structure 110 may be formed using a molding process, for example an automated injection molding process or a compression molding process, in which material for support structure 110 may be manually injected into a mold. Alternatively, support structure 110 may be milled or machined. In such embodiments, the entire support structure 110 may be machined from a blank. Alternatively, support structure 110 may initially be molded and then at least portions of the molded structure machined, for example to provide features that require more precise tolerancing. In certain embodiments, support structure 110 may be further processed after molding and/or machining, although such processing may be done later in the method 200, for example after base optic 115 has been attached or added.

Figure 5:
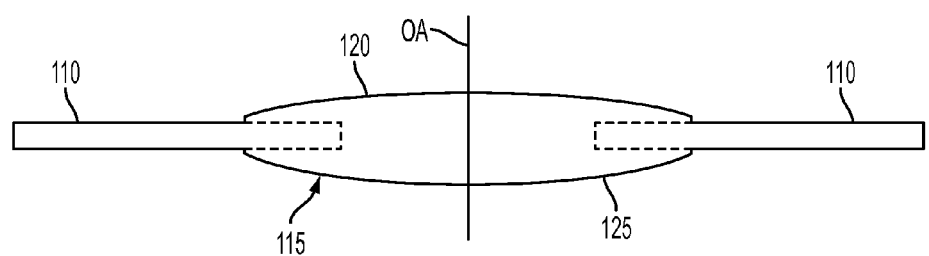
FIG. 5 is a side view of the support structure and a base optic of the intraocular lens shown in FIG. 1.

Referring to FIG. 5, fabrication of intraocular lens 100 next includes element 220 of method 200, comprising forming base optic 115. Base optic 115 may be formed using injection or compressing molding, for example similar to that used to form support structure 110 in element 210. However, in this case support structure 110 is disposed inside the mold so that base optic 115 is formed around support structure 110.

Base optic 115 may be formed of the same material as support structure 110, for example so that both parts form a unitary structure with no detectable boundary between elements 110, 115 and/or to reduce potential for glare at interfaces between materials of dissimilar refractive index. In certain embodiment, base optic 115 is made of a material that is softer, or has a lower modulus or tensile strength, than support structure 110. Such an arrangement is beneficial where intraocular lens 100 is an accommodating intraocular lens in which finished optic 105 changes shape, optical power, and/or axial position in response to an ocular force in order to provide accommodation. Such difference in material or optical properties may be provided by making support structure 110 and base optic 115 from different materials. Alternatively, support structure 110 and base optic 115 may be made from a common polymeric material, but support structure 110 is hardened more than base optic 115, for example by different exposures to a hardening process and/or by adding different concentrations of a hardening or catalytic agent. In certain embodiments, this may be accomplished by using different hydride to vinyl ratios and/or different amounts of a cross-linking agent for each element 110, 115, as discussed in greater detail in U.S. Patent Application Publication Number 2009/0088839, which is hereby incorporated by reference in its entirety.

Fabrication of intraocular lens 100 next includes element 230 of method 200, comprising processing base optic 115 and/or support structure 110. For example, parts 110, 115 may go through an extraction process, such as a Soxhlet extraction process, for removing unwanted impurities. Referring to FIG. 6, an unwanted consequence of the molding and/or extraction processes is that elements 110, 115 may experience uneven shrinkage rates. Uneven shrinkage can affect the surface quality of optical surfaces 120, 125 of base optic 115, resulting in a loss of the optical quality and performance. This may be particularly pronounced near interfaces between base optic 115 and support structure 110.

The surface quality of optical surfaces 120, 125 may be evaluated according to any of the methods used within the art, for example as disclose in various standards such as Mil-O-13830A, Mil-PRF-13830B, ISO 4287, or the like. The surface quality may be expressed in terms of an RMS roughness, where a lower RMS roughness corresponds to higher surface quality. Surface quality may also be expressed in terms of deviations from a desired profile or shape. The surface quality may then be expressed with an average or standard deviation from the desired profile, with a lower deviation corresponding to higher surface quality. In some embodiments, the desired surface shape of surface 120 and/or surface 125 is a sphere having a predetermined radius of curvature. Alternatively, at least one of the surfaces 120, 125 has a surface profile expressed by an equation for a defining a conoid of rotation, wherein a surface sag profile varies according to the relation:

$$\frac{cr^2}{1+\sqrt{1-(1+k)c^2r^2}}$$

where c is a base curvature of the surface portion (which is equal to 1/R, where R is the radius of curvature, k is a conic constant, and r is the radial distance from the optical axis OA. Alternatively, at least one of the surfaces 120, 125 has a surface profile expressed by an equation defining a modified conoid of rotation, wherein a surface sag profile varies according to the relation:

$$\frac{cr^2}{1+\sqrt{1-(1+k)c^2r^2}}+a_4r^4+a_6r^6+\ldots$$

where $a_2, a_4, \ldots$ are constants, c is a base curvature of the surface portion (which is equal to 1/R, where R is the radius of curvature, k is a conic constant, and r is the radial distance from the optical axis OA.

One or more of various metrics may be used in directly expressing, determining, or evaluating the optical quality of base optic 115, finished optic 105, and/or any or all of surfaces 120, 125, 145, 155. For example, the optical quality may be expressed in terms of a Modulation Transfer Function (MTF) performance under certain conditions at one or more spatial frequencies. In some embodiments the MTF value is evaluated at spatial frequencies of 25, 50, or 100 line pairs per mm, for example when base optic 115 or finished optic 105 is evaluated in an eye model including an average cornea. Typical MTF values may include 0.05, 0.10, 0.15, 0.17, 0.20, 0.25, 0.40, 0.55 or higher. Such eye models include, but are not limited to, the Navarro eye model (as published in the journal Optical Sciences of America, Vol. 2, No. 8, pp 1273-1281) or eye model disclosed in TABLE 12, and the associated description, in U.S. Pat. No. 6,609,793 (herein referred to as the "ACE Eye Model"), both of which are incorporated by reference in their entirety.

Other metrics known in the art for expressing, determining, or evaluating the optical quality of optics 105, 115 and/or surfaces 120, 125, 145, 155 include, but are not limited to, MTF volume (integrated over a particular range of spatial frequencies, either in one dimension or in two dimensions), resolution, diopter power, astigmatism, Strehl ratio, encircled energy, RMS spot size, peak-to-valley spot size, RMS wavefront error, peak-to-valley wavefront error, edge transition width, interferometry, wavefront analysis, and resolution by group-element. Additionally or alternatively, any of the following psychophysical metrics may be used: contrast sensitivity, visual acuity, and perceived blur. In addition, other metrics may be found in the literature, such as those detailed in Marsack, J. D., Thibos, L. N. and Applegate, R. A., 2004, "Metrics of optical quality derived from wave aberrations predict visual performance," J Vis, 4 (4), 322-8; Villegas, E. A., Gonzalez, C., Bourdoncle, B., Bonnin, T. and Artal, P., 2002, "Correlation between optical and psychophysical parameters as a function of defocus," Optom Vis Sci, 79 (1), 60-7; van Meeteren, A., "Calculations on the optical transfer function of the human eye for white light," Optica Acta, 21 (5), 395-412 (1974), all of these references being herein incorporated by reference in their entirety. Any or all of the above metrics may be evaluated at a single wavelength, such as 550 nm or any other suitable wavelength, at a plurality of selected wavelengths, or over a spectral region, such as the visible spectrum from 400 nm to 700 nm. The metrics may be weighted over a particular spectral region, such as the weighting associated with the spectral response of the human eye. It will be appreciated that the above criteria may be used in determining or comparing the performance of any of the optic or optic surfaces discussed herein.

Fabrication of intraocular lens 100 also includes element 240 of method 200, comprising fabricating finished optic 105. Referring to FIG. 7, a mold 300 is shown that may be used for fabricating finished optic 100. Mold 300 includes upper and lower portions 310, 315 that join together at parting interface 320. Portions 310, 315 together form a cavity 325 configured to receive support structure 110 and base optic 115. Elements 110, 115 and cavity 325 are shown in FIG. 7 by dashed lines. Mold 300 includes a fixture 330 and associated access port 335 for injecting material into an inner cavity of mold 300. Mold 300 also includes a fixture 340 and associated port 345 for venting overflow material from the inner cavity of mold 300. Finished optic 105 may be formed by compression molding or injection molding.

Mold 300 may be the same mold used to form the base optic 115, or at least have the same, or approximately the same, cavity dimensions as cavity 325 of mold 300. Alternatively, mold 300 may be different from the mold used to form base optic 115 and/or cavity 325 may have different dimensions in the area of the optic than the cavity used to form base optic 115. In some embodiments, different cavity sizes and/or surface profiles are used in forming base optic 115 and finished optic 105, for example, to provide a predetermined thickness of membrane 140 or to provide a final surface profile that is different that that of base optic 115 (e.g., to provide a diffractive surface, multifocal surface, and/or an aspheric surface configured to reduce spherical aberrations).

In some embodiments, the central thickness of the mold used to form base optic 115 is thicker than the central thickness of mold 300 used to form final optic 105. In such embodiments, the central thickness of base optic 115 shrinks after molding, for example as the result of an extraction process to remove impurities. Thus, the central thickness of processed base optic 115 is less than the central thickness of cavity 325 or final optic 105. In this way, the thickness of membrane 140 is less than it would be if the same mold 300 and/or mold cavity 325 were used to form both base optic 115 and final optic 105. In another embodiment, the central thickness of the mold used to form base optic 115 is thinner than the central thickness of mold 300 used to form final optic 105. Such an embodiment may be used to form a membrane 140 thickness that is greater than would result if the same mold 300 and/or mold cavity 325 were used to form both base optic 115 and final optic 105.

Fabrication of finished optic 105 may be used to correct deviations in the surface profile and/or optical performance of surfaces 120, 125 of base optic 115. Additionally or alternatively, fabrication of finished optic 105 may serve other purposes. Such purposes include modification or enhancement of the shape or profile of at least one of the surfaces 120, 125. For example, element 240 of method 200 may include altering or modifying surfaces 120 and/or 125 to provide an aspheric shape or profile for correcting a monochromatic aberration of lens 100 and/or an aberration of an eye into which intraocular lens 100 is placed. The resulting outer surface 145 and/or 155 may be configured to correct a monochromatic aberration such as a spherical aberration, an astigmatism, coma, trefoil, or the like. Additionally element 240 of method 200 may include altering surfaces 120 and/or 125 to provide a refractive multifocal profile, altering surfaces 120 and/or 125 to provide a monofocal or multifocal diffractive profile (e.g. to correct a chromatic aberration, produce multiple foci, and/or provide an extended depth of focus), or the like.

In certain embodiments, method 200 is used to produce a shell 135 that include both anterior and posterior membranes 140, 150. Alternatively, method 200 may be used to provide only anterior membrane 140 or only posterior membrane 150. For example, the anterior surface of finished optic may contain only anterior membrane 140, while posterior surface 125 is of sufficient quality that posterior membrane 150 is unnecessary. Alternatively, one of the surfaces of finished optic 105 may comprise a surface of a second optic, as discussed in greater detail above.

Fabrication of finished optic 105 results in membranes or films 140 and 150 that are relatively thin. Generally, the thickness of membranes 140, 150 are each less than or equal to about 0.2 mm or less than or equal to 15% of the total center thickness of finished optic 105, preferably less than or equal to 10% of the total center thickness of finished optic 105. For example, in one embodiment, the center thickness of finished optic 105 is about 2.0 millimeters and the thickness of each film 140, 150 is 0.15 mm, or about 7.5% of the center optic thickness. As used herein, the term "about", when used in the context of a linear measurement in millimeters, means within ±0.1 mm if the measurement is given to the first decimal point and within ±0.01 mm if the measurement is given to the second decimal point. In an embodiment, the center thickness of finished optic 105 is less than or equal to 2.5 mm.

Fabrication of intraocular lens 100 may optionally include element 250 of method 200, comprising processing finished optic 105. For example, processing of finished optic 105 may include an additional extraction process to remove contaminants from membranes 140, 150. In such embodiments, the relatively thin membrane reduces or eliminates the amount of shrinkage of the membranes 140, 150 that occurs during extraction. Accordingly, the thickness of the membrane after processing is generally less than 0.25 mm, preferably less than 0.20 mm, and even more preferably less than or equal to 0.15 mm or even 0.10 mm. A lower limit on the thickness of membranes 140, 150 exists that depends on such considerations as the amount of variation or RMS roughness of surfaces 120, 125 of base optic 115, as well as on practical fabrication considerations such as how thin a layer may be injected into a mold used to form finished optic 105. In an embodiment, the thickness of membranes 140, 150 may vary around base optic 115 depending upon the shape and surface features of base optic 115 yielding portions or sections of membranes 140, 150 that have a thickness greater than 0.25 mm, but the average thickness of the entire membrane 140, 150 is less than or equal to 0.25 mm. For example, base optic 115 may have an undulating (wavy) surface where a portion of membrane 140, 150 is thicker than 0.25 mm, but the average thickness over the entire extent of membrane 140, 150 is less than or equal to 0.25 mm.

Method 200 may include additional elements. For example, element 240 and/or element 250 may be repeated. For example, once an optic is formed in element 240 to provide membranes 140 and/or 150, intraocular lens 100 may again be placed inside mold 300, or a different mold, to increase the thickness, smoothness, or optical quality of membranes 140, 150 and finished optic 105. Between placements into mold 300, or another mold, the newly formed optic may be processed according to element 250 or otherwise processed. Element 240 of method 200 may be repeated with one or more molds as many times as necessary to provide a desired surface characteristic, optical characteristic, and/or optical quality. In some embodiments, the entirety, or at least the majority, of either or both outer surfaces 145, 155 may be formed using this repeated molding procedure. Alternatively, only selected portions of either or both outer surfaces 145, 155 may be formed using this repeated molding procedure, for example, to produce a different optical characteristic or optical quality of a central portion of finished optic 105 as compared to a peripheral portion of finished optic 105.

For the illustrated embodiment shown in FIG. 3, the thickness or average thickness of membranes 140, 150 is constant, or approximately constant (e.g., due to surface variations or RMS roughness of surfaces 120, 125 of base optic 115), with radius from optical axis OA. In certain embodiments, the thickness or average thickness of membrane 140 and/or membrane 150 varies with radius from optical axis OA. For example, the thickness at the center or optical axis OA of the finished optic 105 is thicker that at the periphery of finished optic 105. Such thickness variation may advantageously aid the final molding process to form finished optic 105 and/or result in an overall or average membrane thickness that is thinner than if a uniform membrane thickness were used.

Experimental results have shown that the method 200 can be used to provide an intraocular lens, such as the intraocular lens 100, that has an optical quality that is significantly better than an intraocular lens that is substantially the same, but made without a membrane or film, such as the film 140. For example, it has been found that when intraocular lens 100 is made according to all of the elements of method 200, the resulting finished optic 105 may have an MTF value (at a spatial frequency of 50 line pairs per mm and an aperture of 5 mm) that is at least twice that of a reference intraocular lens made of the same material and/or mold (e.g., mold 300), wherein the reference intraocular lens is made using only elements 210-230 of method 200 (e.g., to produce the base optic 115 shown in FIG. 6). Generally, the MTF value (at a spatial frequency of 50 line pairs per mm and an aperture of 5 mm) of finished optic 105 is at least 10% higher than a that of a reference intraocular lens made of the same material and/or mold (e.g., mold 300) and using only elements 210-230 of method 200, the reference intraocular lens having the same optical power, or the same optical power to within ±2 Diopters, as finished optic 105. Preferably, the MTF value (at a spatial frequency of 50 line pairs per mm and an aperture of 5 mm) of finished optic 105 is at least 25% higher, 50% higher, 100% higher, or even 200% higher than that of such a reference intraocular lens.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An intraocular lens, comprising:
   a finished optic comprising:
      a base optic having an anterior surface and an opposing posterior surface, at least one of the surfaces having a first value of a surface quality parameter; and
      a membrane including an inner surface and an outer surface, the inner surface covering one or more of the surfaces of the base optic, the outer surface having a second value of the surface quality parameter, the second value being greater than the first value, wherein the outer surface defines a plurality of echelettes comprised of a diffractive grating,
      wherein the base optic has a first refractive index at a wavelength within the visible spectrum and the membrane has a second refractive index at the wavelength, the first refractive index being unequal to the second refractive index; and
   a support structure coupled to the finished optic, wherein the support structure includes a protruding portion disposed within the base optic configured to allow ocular forces to be transferred to a central portion of the base optic, and further wherein the protruding portion is refractive.

2. The intraocular lens of claim 1, wherein the base optic and the membrane are integrally formed.

3. The intraocular lens of claim 1, wherein the base optic and the membrane has the same modulus.

4. The intraocular lens of claim 1, wherein the base optic is made from a first material having a first value of a property and the membrane is made from a second material having a second value of the property, the first value being greater than or less than the second value.

5. The intraocular lens of claim 4, wherein the property is one or more of stiffness, tensile strength, modulus, lubricity, or tackiness.

6. The intraocular lens of claim 4, wherein the values differ by at least 2%.

7. The intraocular lens of claim 4, wherein the values differ by at least 5%.

8. The intraocular lens of claim 1, wherein the quality parameter is selected from the group consisting of surface smoothness, surface accuracy, and modulation transfer function.

9. The intraocular lens of claim 1, wherein the support structure comprises one or more haptics.

10. The intraocular lens of claim 1, wherein the base optic has a first refractive index at a wavelength within the visible spectrum and the protruding portion has a second refractive index at the wavelength, the first refractive index being about equal to the second refractive index.

11. The intraocular lens of claim 1, wherein the base optic has a first refractive index at a wavelength within the visible spectrum and the protruding portion has a second refractive index at the wavelength, the first refractive index being unequal to the second refractive index.

12. The intraocular lens of claim 1, wherein the base optic has a first refractive index at a wavelength within the visible spectrum and the membrane has a second refractive index at the wavelength, the first refractive index being about equal to the second refractive index.

13. The intraocular lens of claim 1, wherein the base optic has a first refractive index at a wavelength within the visible spectrum, the membrane has a second refractive index at the wavelength, the protruding portion has a third refractive index at the wavelength, the refractive indices being about equal to one another.

14. The intraocular lens of claim 1, wherein the base optic and the membrane is made of a common polymeric material.

15. The intraocular lens of claim 1, wherein the membrane is made of a different material than the base optic.

16. The intraocular lens of claim 1, wherein the base optic comprises a peripheral edge joining the anterior surface of the base optic to the posterior surface of the base optic.

17. The intraocular lens of claim 16, wherein the finished optic comprises a wall portion disposed over at least a portion of the peripheral edge of the base optic.

18. The intraocular lens of claim 16, wherein the finished optic comprises a first membrane disposed over the anterior surface of the base optic and a second membrane disposed over the posterior surface of the base optic, the wall portion joining the first membrane and the second membrane along circumferential portions of the membranes.

19. The intraocular lens of claim 1, wherein the membrane has a thickness that is less than or equal to 0.15 millimeters.

20. The intraocular lens of claim 1, wherein the membrane has a thickness that is less than or equal to 10% of an axial thickness of the finished optic along the optical axis.

21. The intraocular lens of claim 1, wherein the protruding portion is disposed along a line parallel to the optical axis within a peripheral portion of the finished optic.

22. The intraocular lens of claim 1, wherein the diffractive grating is monofocal.

23. The intraocular lens of claim 1, wherein the diffractive grating is multifocal.

* * * * *